US012193652B2

(12) United States Patent
Mohanty

(10) Patent No.: US 12,193,652 B2
(45) Date of Patent: Jan. 14, 2025

(54) ORAL BIOPSY INSTRUMENT WITH LIVE CAMERA AND FIBER OPTIC LIGHT

(71) Applicant: Siksha 'O' Anusandhan, Bhubaneswar, Bhubaneswar (IN)

(72) Inventor: Neeta Mohanty, Bhubaneswar (IN)

(73) Assignee: Siksha 'O' Anusandhan, Bhubaneswar (IN)

( * ) Notice: Subject to any disclaimer, the term of this patent is extended or adjusted under 35 U.S.C. 154(b) by 1322 days.

(21) Appl. No.: 16/584,962

(22) Filed: Sep. 27, 2019

(65) Prior Publication Data

US 2020/0100777 A1 Apr. 2, 2020

(30) Foreign Application Priority Data

Oct. 1, 2018 (IN) .............................. 201831037016

(51) Int. Cl.
*A61B 10/02* (2006.01)
*A61B 1/00* (2006.01)
*A61B 1/04* (2006.01)
*A61B 1/24* (2006.01)
*A61B 90/00* (2016.01)
*A61B 90/30* (2016.01)

(52) U.S. Cl.
CPC ...... *A61B 10/0266* (2013.01); *A61B 1/00009* (2013.01); *A61B 1/00087* (2013.01); *A61B 1/04* (2013.01); *A61B 1/24* (2013.01); *A61B 2010/0208* (2013.01); *A61B 2090/062* (2016.02); *A61B 2090/0813* (2016.02); *A61B 90/30* (2016.02); *A61B 2090/306* (2016.02); *A61B 2090/309* (2016.02); *A61B 2560/0462* (2013.01)

(58) Field of Classification Search
CPC .......... A61B 10/0266; A61B 2090/306; A61B 2090/309; A61B 2010/0208
See application file for complete search history.

(56) References Cited

U.S. PATENT DOCUMENTS

| 5,848,978 | A | 12/1998 | Genx | |
|---|---|---|---|---|
| 2003/0181823 | A1* | 9/2003 | Gatto | A61B 10/04 600/564 |
| 2004/0097920 | A1* | 5/2004 | Desinger | A61B 10/0266 606/45 |
| 2007/0232954 | A1 | 10/2007 | Harris et al. | |
| 2009/0018467 | A1 | 1/2009 | Chiu et al. | |
| 2015/0126903 | A1* | 5/2015 | Wang | A61B 10/0266 600/567 |

* cited by examiner

*Primary Examiner* — Daniel L Cerioni
(74) *Attorney, Agent, or Firm* — MDIP LLC

(57) ABSTRACT

This invention relates to a high precision biopsy instrument which is self-cutting and self-retrieval in nature and includes a camera and a fiber-optic light configured for obtaining the biopsy tissue. The biopsy instrument with the incorporation of vertical and horizontal cutting blades is configured to obtain the biopsy tissue with minimum architectural tissue damage. The camera in the biopsy instrument is used to facilitate capturing photographs of the potentially malignant disorders and malignant neoplasms for the purpose of diagnosis as well as video graph the same for the purpose of determining the exact site of biopsy through tele-conferencing between surgeons and pathologists. The pictures obtained during the procedures can be used for documentation purpose. The present invention also includes a fiber optic light for illumination of the operating site as it creates less colour variation.

10 Claims, 3 Drawing Sheets

ORAL BIOPSY INSTRUMENT WITH LIVE CAMERA AND FIBER OPTIC LIGHT

CROSS REFERENCE TO RELATED APPLICATIONS

This application claims priority to Indian Patent Application No. 201831037016 filed 1 Oct. 2018, entitled Oral Biopsy Instrument with Live Camera and Fiber Optic Light, herein incorporated by reference in its entirety.

FIELD OF THE INVENTION

The present invention relates to a biopsy instrument which includes a camera and a fiber optic light configured for obtaining the biopsy tissue. More particularly, the present invention relates to a high precision biopsy instrument including a live camera included in the biopsy instrument which is self-cutting and self-retrieval in nature and is used for obtaining the biopsy tissue.

BACKGROUND OF THE INVENTION

India Application titled, "Biopsy Instrument (Self-Cutting And Self-Retrieval)," App. No. 201831003054, was filed on Jan. 25, 2018, and also assigned to "Siksha 'O' Anusandhan, Bhubaneswar" and has the same inventor, "Dr. Neeta Mohanty," which is incorporated herein by reference in entirety.

Oral tissue biopsy may be necessary for lesions that cannot be diagnosed on the basis of the history and clinical findings alone. Approximately 10% of patients who are examined have some abnormality of the oral mucosa. Biopsy is often the definitive procedure that provides tissue for microscopic analysis when additional information is required to guide any indicated therapy.

Punch biopsy is the most commonly used procedure for obtaining the tissue sample for biopsy where the tissue is first cut with the circular blade of the manual biopsy instrument. Then the retrieval of the tissue is done by holding it with toothed forceps and cutting it from below. During the handling of the tissue with the toothed forceps, there may be architectural tissue damage.

The site of the biopsy and depth of the biopsied tissue are two critical determinants for correct histopathological diagnosis of oral diseases especially potentially malignant disorders and malignant oral neoplasms. In fact, the biopsy instrument with an in-built camera would accelerate the process of diagnosis through teleconferencing amongst multiple clinicians and pathologists. However, none of the existing prior art discloses a biopsy instrument having an in-built camera.

In the prior art, US Pub No 20070232954 discloses an automatic skin biopsy device that includes a drive unit and a variety of shapes and sizes of disposable cartridges. The device is capable of automatic extraction of a small and precisely located portion of skin having a shape similar to a wide canoe. A disposable cartridge is mounted onto and driven by the drive unit which incorporates at least one gear motor. In a preferred embodiment, the gear motor in the drive unit drives, via gears and cams, two cutter blades in the disposable cartridge through separate curved paths to extract from the skin the generally wide canoe-shaped skin sample. Preferably another gear motor via gear and cam action produces back and forth oscillation of the blades to assure easy slicing of the skin tissue. The canoe-shape incision that is about 1 to 4 mm deep produces a good biopsy sample and the incision is easily closed with a medical staple or sutures. In preferred embodiments a stapler is provided as a part of the sample acquisition device. Materials used to fabricate the driver and the cartridge preferably transparent to permit accurate placement of the incision.

In another prior art, U.S. Pat. No. 5,848,978, a surgical core biopsy apparatus is disclosed, wherein the surgical core biopsy apparatus is having a hollow elongated member with an axis and a leading end, a sharpened edge at a portion of the leading end for cutting tissue along the axis, an actuator, and a cutting edge, linked to the actuator, being movable along a path including a transverse component to the axis, effective for severing tissue along the path. The path is preferably an arcuate path, the cutting device being pivoted about an axis transverse to the axis of said hollow elongated member at the said leading end. The actuator preferably acts by way of a compression force transmitted along the axis by a compression member, from a handle portion to the cutting edge. The elongated member is preferably a tube having two or more lumens, a first large centrally located lumen for accommodating a tissue core sample, and at least one other eccentrically located rectangular cross section lumen containing the compression member. The biopsy apparatus may be used, for example, to obtain a percutaneous excision breast biopsy from a tumor whose location is marked with a radiopaque guide wire.

Another prior art, US Pub No 20090018467, discloses a punch biopsy apparatus for removing all or a portion of a suspect dermal growth. A punch biopsy apparatus has: a hollow cylinder body; a coring blade at the base of the hollow cylinder body; at least one scooping blade pivotally secured by an axle and a pair of pivot seats within the cylinder body, where each scooping blade is semicircular, a longitudinally-moveable plunger secured within the hollow cylinder, where the plunger has at least one plunger leg for contacting each scooping blade, and each plunger leg transfers longitudinal plunger movement to its respective scooping blade, thereby causing rotational scooping-blade movement. This device helps minimize bleeding and minimize damage to the biopsy sample being retrieved.

Another prior art, WO2013166443, discloses a punch biopsy tool having a punch cutting element which includes an inner surface, an outer surface, and a cutting edge along a bottom edge, and which defines an aperture between the inner surface and the outer surface. The punch biopsy tool also includes a flexible cutting element which is disposed along the inner surface of the punch cutting element and is configured to be pulled through the aperture.

Hence, it is apparent that a need exists for a technique that decimates the above-mentioned problems of the prior art and provides an improved method and apparatus for performing oral biopsy.

The applicant has devised, tested and embodied the present invention to overcome the shortcomings of the state of the art and to obtain these and other purposes and advantages.

OBJECTIVE OF THE INVENTION

The principal objective of the invention is to provide a biopsy instrument which includes a camera and a fiber optic light configured for obtaining the biopsy tissue. The other objective of the invention is to provide a high precision biopsy instrument which is self-cutting and self-retrieval in nature and is used for obtaining the biopsy tissue precisely, efficiently, and using user friendly techniques.

According to another objective of the invention, a live camera is included in the biopsy instrument which will help to decide the exact site of biopsy.

Yet another objective of the invention is to enable the clinician to capture real-time images of the lesion or growth with the help of the camera which will help the pathologist to correlate during diagnosis.

The other objective of the invention is to include a fiber optic light for illumination of the operating site as it creates less colour variation.

SUMMARY OF THE INVENTION

This invention relates to a biopsy instrument which includes a camera and a fiber optic light configured for obtaining the biopsy tissue. The present invention discloses a high precision biopsy instrument which is self-cutting and self-retrieval in nature and is used for obtaining the biopsy tissue. The present invention will have a live camera included in the biopsy instrument which will help to decide the exact site of biopsy with the coordination of the pathologist and the operating personnel. This invention also includes a camera which can be attached to the computer and can be used to capture the image of the lesion or growth which can be transferred to the pathologist to confirm the site of biopsy. The invention also enables the clinician to capture the image of the lesion or growth with the help of the camera which will help the pathologist to correlate during diagnosis.

The camera in the biopsy instrument is used to facilitate capturing photographs of the potentially malignant disorders and malignant neoplasms for the purpose of diagnosis as well as video graph the same for the purpose of determining the exact site of biopsy through tele-conferencing between surgeons and pathologists. The pictures obtained during the procedures can be used for documentation purpose. The present invention also includes a fiber optic light for illumination of the operating site as it creates less colour variation. This invention provides an instrument which is precise, efficient, user friendly and helps to decide the exact site of biopsy for giving the final histopathological diagnosis.

BRIEF DESCRIPTION OF THE ACCOMPANYING DRAWINGS

DETAILED DESCRIPTION OF THE PREFERRED EMBODIMENTS

Figure 1:
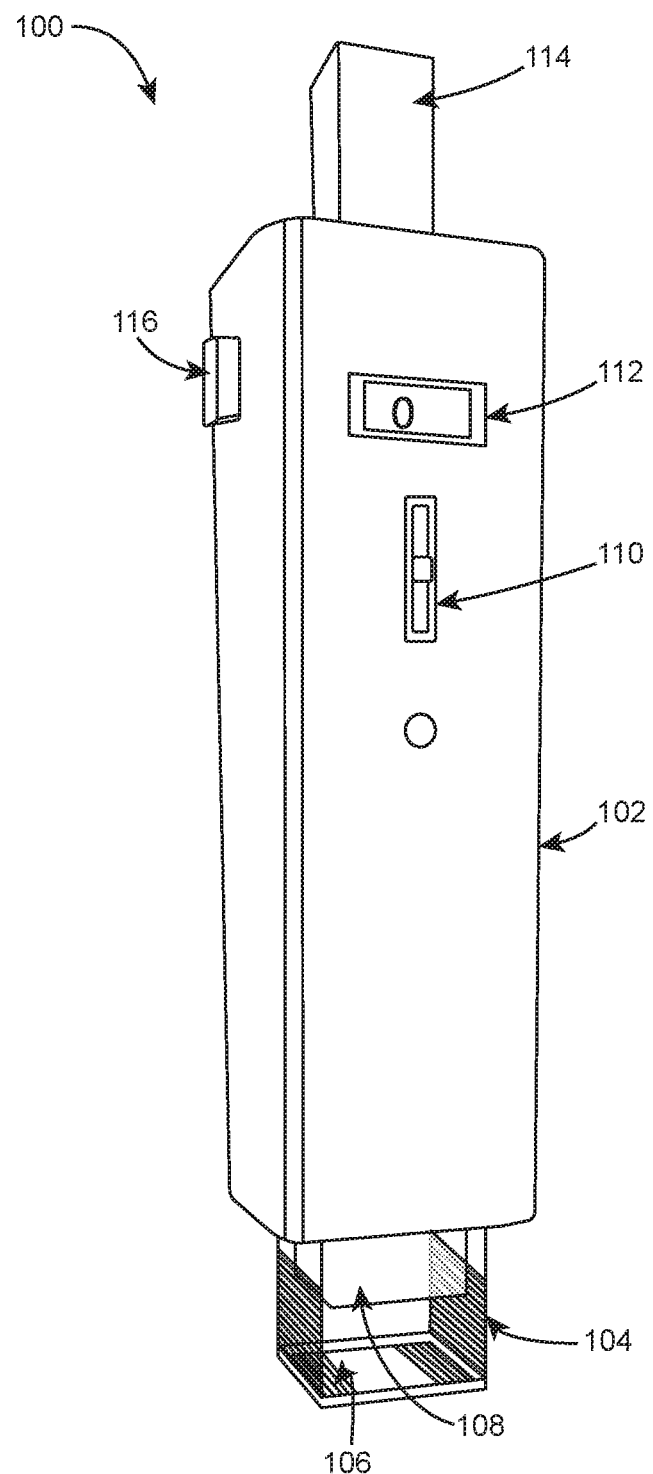
FIG. 1 illustrates an exemplary self-cutting and retrieval oral biopsy instrument where various embodiments of the present invention are implemented.

This invention relates to improvements in self-cutting and retrieval biopsy instruments. This biopsy instrument is intended for use in connection with punch presses and is for the purpose of cutting the tissue without the twisting action.

One object of the present invention is to provide a very simple, easy to operate but effective form of biopsy instrument and said biopsy instrument being substantially self-contained in its construction, but, being provided with suitable means whereby its movable blades may be operatively connected to a drive shaft of the punch press to cause proper functioning of the said instrument.

The biopsy instrument for obtaining the biopsy tissue comprises a camera and a fiber optic light. The biopsy instrument is highly precise, efficient, user friendly, and self-cutting and self-retrieval in nature. The camera in the biopsy instrument helps to decide the exact site of biopsy with the coordination of the pathologist and the operating personnel. The camera can be attached to the computer and can be used to capture the image of the lesion or growth which can be transferred to the pathologist to confirm the site of biopsy. The fiber optic light in the instrument is used for illumination of the operating site as it creates less colour variation.

A further feature of the present invention consists in the provision of digital caliper means. The punch cutting blades are digitally callipered and the speed is controlled with the help of a motor to ensure more accurate and precise tissue cutting. With the help of this instrument, a depth of the tissue ranging from 3 mm to 8 mm can be obtained as per the requirement.

The punch biopsy instrument further comprises a horizontal cutting element which is placed along the inner surface of the punch cutting element and is configured to detach the final biopsy tissue from the underlying tissue after the desired depth of the tissue is punched. This procedure helps to eliminate the requirement of handling of the tissue with toothed forceps thereby preventing any architectural damage to the obtained tissue.

Although the foregoing description of the present invention has been shown and described with reference to particular embodiments and applications thereof, it has been presented for purposes of illustration by way of examples and description and is not intended to be exhaustive or to limit the invention to particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should, therefore, be seen as being within the scope of the present invention as determined by the appended claims when interpreted in accordance with the breadth to which they are fairly, legally, and equitably entitled. The biopsy instrument includes a camera and a fiber optic light and will be configured for obtaining the biopsy tissue. The instrument will have very high precision and will be self-cutting and self-retrieval in nature. The instrument will have a live camera included in the biopsy instrument which will help to decide the exact site of biopsy with the coordination of the pathologist and the operating personnel. The biopsy instrument will also include a camera which can be attached to the computer and can be used to capture the image of the lesion or growth which can be transferred to the pathologist to confirm the site of biopsy. The instrument will also include a fiber optic light for illumination of the operating site as it creates less colour variation.

FIG. 1 illustrates an exemplary self-cutting and retrieval oral biopsy instrument 100 where various embodiments of the present invention are implemented. The biopsy instrument 100 comprises one handle (body or main frame) to which a vertical blade, sliding blades and a piston are attached as described in more details below.

The self-cutting and retrieval oral biopsy instrument 100 comprises a body 102 (i.e. main frame or handle), vertical blade 104, horizontal cutting element 106, piston 108, vertical blade control 110, depth indicator 112, horizontal control 114, and piston control 116.

The body 102 of the biopsy instrument 100 has a width which can range preferably from 1 cm to 2 cm and length with range preferably from 10 cm to 14 cm. However, the embodiments of the present invention may be applied to various combinations of width and length of the body 102. The shape of body 102 may be cylindrical, cuboid, etc. without limiting the scope of the invention.

The vertical blade 104 is the punch cutting element with an inner surface, an outer surface and a cutting edge along the bottom surface including a hollow space between the inner surfaces where the desired tissue is punched. The cross-section of the vertical blade is square in shape. The width of the blades of each side is 5 mm which is fixed. This blade can be adjusted up and down and set at the desired cutting depth ranging from 3 mm to 8 mm. Once the blade has been set to the desired depth value, it remains fixed with the main frame for the initial vertical punch.

The horizontal cutting element 106 is placed along the inner surface of the punch cutting element and is configured to detach the final biopsy tissue from the underlying tissue after the desired depth of the tissue is punched with minimum tissue architectural damage. The horizontal cutting element 106 includes preferably two sliding/retractable blades configured along the inner side of the vertical blade. After punching the tissue using the vertical blade 104, the horizontal blades slide down and at the edge move at an angle of 90° to the vertical blade, cutting the specimen tissue from below, and holding it inside the hollow space. According to an exemplary embodiment, the cutting edges of the vertical blade and/or sliding blade are made up of surgical steel.

After bringing the specimen to the desired location for release, the cutting blades slides back to their initial position by releasing a lever (not shown). Attached to the lever the piston 108 moves down in a reverse movement mechanism (e.g. moving downwards & then moving upwards) to push the specimen out of the hollow space placing it in formal saline for further procedure.

The vertical blade control 110 is used to adjust the depth of the tissue to be cut precisely ranging from 3 mm to 8 mm. The desired depth of the biopsy specimen can be predetermined using the vertical blade control 110 depending on the type of oral lesion.

The depth indicator 112 displays the depth of the tissue to be cut set by vertical blade control 110.

The horizontal control 114 is used to control the movement of sliding blades which are placed along the inner surface of the vertical blade 104. When the retractable horizontal control 114 is moved from first position to second position (e.g. pressed down), the horizontal cutting blades slide down along the inner side of the vertical cutting blade and at the edge move at an angle of 90 degree to the longitudinal axis of the vertical blade, cutting the specimen tissue from below and holding it inside the hollow space. When the horizontal control 114 is moved back to first position from the second position, the sliding blades retract back to the initial position along the inner surface of the vertical blade 104. It shall be noted by the person skilled in the art that the mechanism to engage the horizontal cutting blades, as depicted herein, is for the illustration purpose only, and any other suitable method known in the art may be deployed without any limitation to engage the horizontal cutting blades.

The piston control 116 is used to control the movement of the piston 108. The piston control 116 is used to move piston 108 down in a reverse movement mechanism which pushes the specimen tissue out of the hollow space placing it in formal saline for further procedure.

Figure 2:
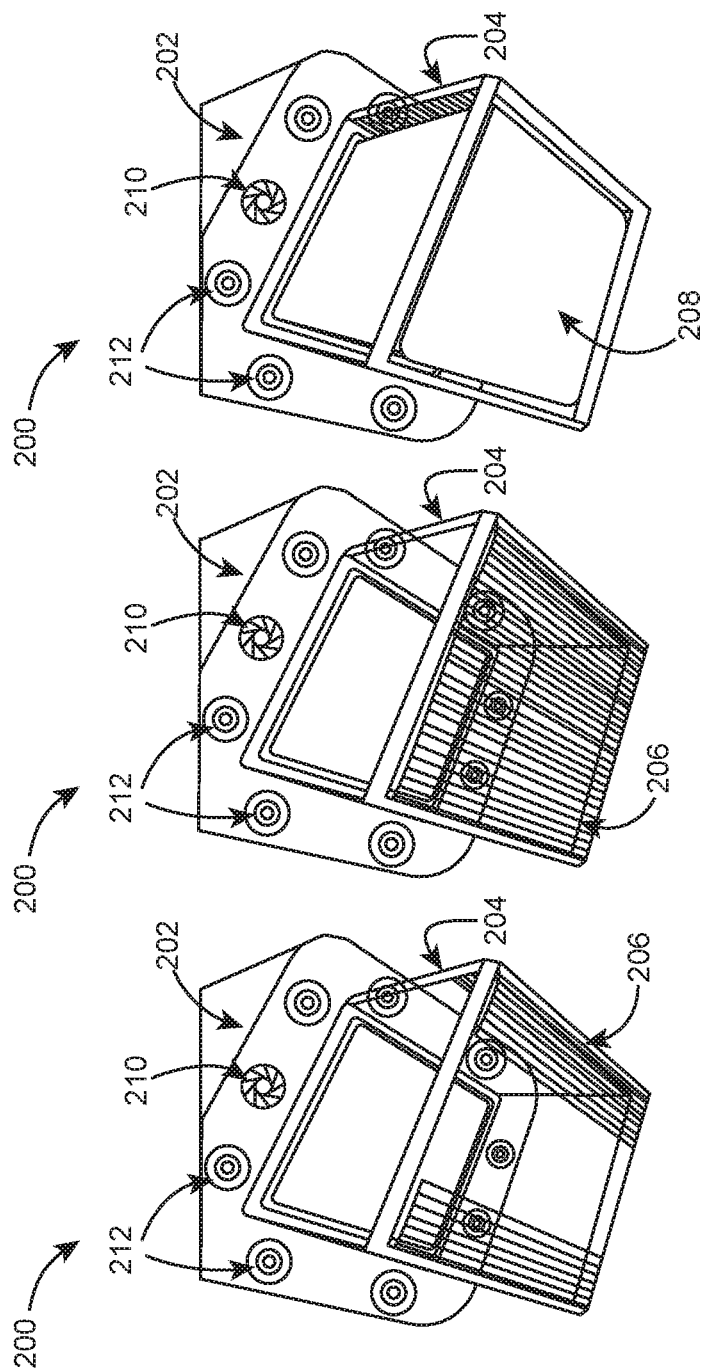
FIG. 2(a) illustrates the bottom-view of the self-cutting and retrieval oral biopsy instrument according to an embodiment of the present invention.
FIG. 2(b) illustrates the sliding blades of the horizontal cutting element in closed position during the cutting procedure of the specimen tissue according to an embodiment of the present invention.
FIG. 2(c) illustrates the downward movement of piston according to an embodiment of the present invention.

FIG. 2(a) illustrates the bottom-view of the self-cutting and retrieval oral biopsy instrument 200. The bottom of the body 202 comprises vertical blade 204, horizontal cutting element 206, camera 210 and light sources 212 (e.g. fiber optic lights and/or light-emitting-diodes (LEDs)). FIG. 2(a) illustrates the sliding blades of the horizontal cutting element 206 moving down at an angle of 90° to the vertical blade 204.

According to an embodiment, the vertical blade can be dismantled from the body of the biopsy instrument for sterilization purposes. According to another embodiment, the retractable/sliding blades can be dismantled for the sterilization purposes.

FIG. 2(b) illustrates the sliding blades of the horizontal cutting element 206 in closed position during the cutting procedure of the specimen tissue.

FIG. 2(c) illustrates the downward movement of piston 208 which releases the specimen out of the hollow space and placing it in formal saline.

According to an embodiment of the present invention, the oral biopsy instrument 200 may have one or more camera 210. The camera 210 is positioned besides the fiber optic lights 212 on the bottom of the body 202. In an alternate aspect of the embodiment of the invention, the camera 210 can be positioned inside the piston 208.

Figure 3:
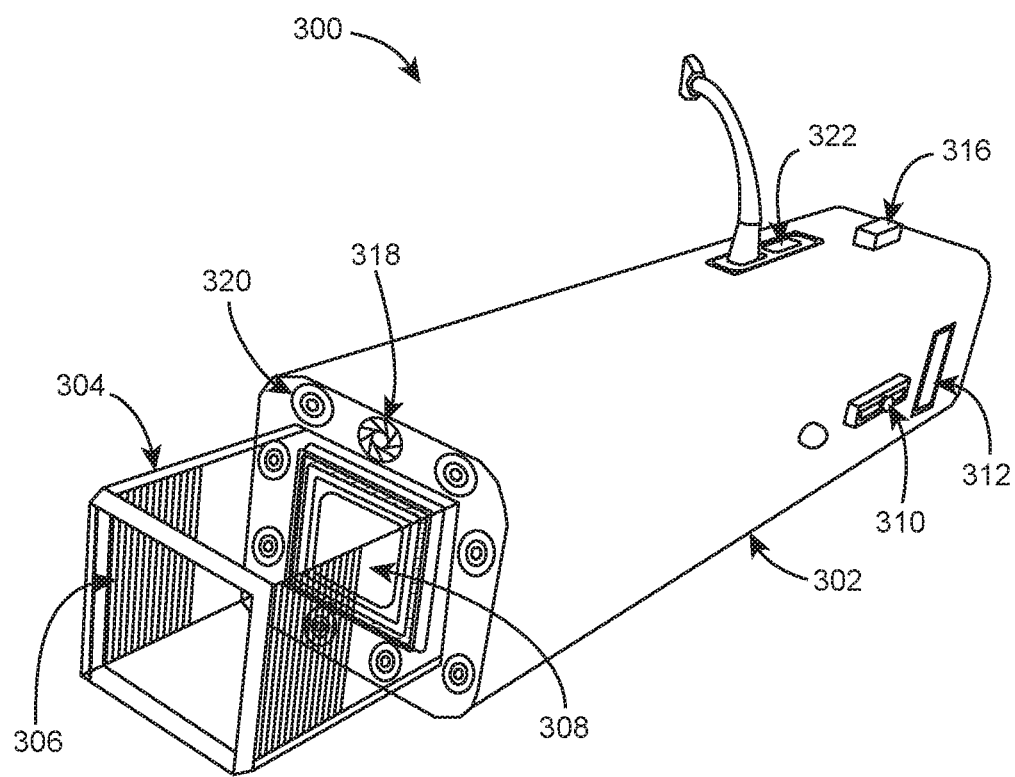
FIG. 3 illustrates an exemplary self-cutting and retrieval oral biopsy instrument with a communication module along with the camera and fiber optic light according to an embodiment of the present invention.

FIG. 3 illustrates yet another embodiment of the invention. The self-cutting and retrieval oral biopsy instrument 300 comprises a body 302, vertical blade 304, horizontal cutting element 306, a piston 308, vertical blade control 310, depth indicator 312, piston control 316, camera 318, fiber optic lights 320, and a communication module 322. The communication module 322 is used to transfer live stream data from oral biopsy instrument 300 to a computing device for example, a Personal Computer (PC), a desktop computer, a mobile computer, a laptop computer, a notebook computer, a tablet computer, an Ultrabook™ computer, a server computer, a handheld computer, a handheld device, a Personal Digital Assistant (PDA) device, a handheld PDA device, a mobile or portable device, a wireless communication device, and the like. The communication module 322 transfers data using wired or wireless mode. In an embodiment, the wired communication mode can be, such as, without limitation, USB, Ethernet, Fiber-optic cable, co-axial cable, or the like. The wireless mode of communication can be, such as, without limitation, Bluetooth, WLAN, Wi-Fi, RF communication, infrared communication, cellular communication e.g. 2G, 3G, 4G LTE, 5G, or the like.

For example, in an embodiment, the camera can be attached to the computer using the wired or wireless communication modes and can be used to capture real-time images of the lesion or growth which can be transferred to the pathologist to confirm the site of biopsy.

According to an embodiment of the present invention, the biopsy instrument may be arranged in shapes such as, but not limited to, angular shape, L-shape, or the like, which makes it easier to access obscure or inaccessible areas in the oral cavity.

It shall be apparent to the person skilled in the art that the invention is described in reference to oral biopsy, but it shall not be considered limiting and many changes and modifications may be made within the scope of the embodiments herein, without departing from the spirit and scope thereof, and the embodiments herein include all such modifications.

Although the present disclosure has been described in terms of certain preferred embodiments, various features of separate embodiments can be combined to form additional embodiments not expressly described. Moreover, other embodiments apparent to those of ordinary skill in the art after reading this disclosure are also within the scope of this invention. Furthermore, not all of the features, aspects and advantages are necessarily required to practice the present disclosure. Thus, while the above detailed description has shown, described, and pointed out novel features of the invention as applied to various embodiments, it will be understood that various omissions, substitutions, and changes in the form and details of the apparatus or process illustrated may be made by those of ordinary skill in the technology without departing from the spirit of the invention. The inventions may be embodied in other specific forms not explicitly described herein. The embodiments described above are to be considered in all respects as illustrative only and not restrictive in any manner.

I claim:

1. An oral biopsy instrument comprising:
   a punch cutting element with an inner surface, an outer surface and a cutting edge along a bottom surface, wherein said punch cutting element forms a hollow space enclosed by said inner surface;
   a horizontal cutting element comprising one or more retractable blades placed along the inner surface of the punch cutting element, wherein the retractable blades are configured to move from a first position to a second position to detach and hold a final biopsy tissue from an underlying tissue after a desired cutting depth is punched, and to retract back from the second position to the first position to release the final biopsy tissue, wherein in said first position, said one or more retractable blades are placed along said inner surface of said punch cutting element, and in said second position, said one or more retractable blades enclose said bottom surface to securely hold said final biopsy tissue in said hollow space;
   a camera configured to capture real time images of a biopsy site; and
   a light source for illuminating the biopsy site.

2. The biopsy instrument of claim 1, wherein the camera is further configured to locate an exact location of the biopsy site by capturing an image of a lesion or growth, wherein the captured image is transferred to a pathologist to confirm the biopsy site.

3. The biopsy instrument of claim 1, wherein the light source is operably connected with the camera and is configured for illumination of the biopsy site.

4. The biopsy instrument of claim 1, wherein the punch cutting element is arranged to dismantle from a handle for performing sterilization.

5. The biopsy instrument of claim 1, wherein the one or more retractable blades are arranged to dismantle from the inner surface of the punch cutting element for performing sterilization.

6. The biopsy instrument of claim 1, wherein the one or more retractable blades move at an angle of at least 90 degrees relative to a longitudinal axis of the vertical blade to detach the final biopsy tissue from the underlying tissue after the desired cutting depth is punched.

7. The biopsy instrument of claim 1 further comprises a piston which is configured to release the final biopsy tissue by making a downward movement along with simultaneous retraction of the one or more retractable blades from the second position to the first position.

8. The biopsy instrument of claim 1 further comprises a piston which is configured to move back to its original position in a reverse movement mechanism, by using a piston control, after releasing the final biopsy tissue.

9. The biopsy instrument of claim 1, wherein the light source comprises one or more fiber-optic lights and/or light emitting diodes (LEDs).

10. The biopsy instrument of claim 1 is an oral biopsy instrument which is configured to detach the final biopsy tissue from the underlying tissue in an oral cavity.

* * * * *